US006761166B2

(12) United States Patent
Ahlmen et al.

(10) Patent No.: US 6,761,166 B2
(45) Date of Patent: Jul. 13, 2004

(54) DEVICE FOR REDUCING DEAD SPACE IN A VENTILATOR SYSTEM

(75) Inventors: Christer Ahlmen, Sollentuna (SE); Magnus Hallback, Bromma (SE)

(73) Assignee: Maquet Critical Care AB, Solna (SE)

( * ) Notice: Subject to any disclaimer, the term of this patent is extended or adjusted under 35 U.S.C. 154(b) by 0 days.

(21) Appl. No.: 10/342,058

(22) Filed: Jan. 14, 2003

(65) Prior Publication Data

US 2003/0131665 A1 Jul. 17, 2003

(30) Foreign Application Priority Data

Jan. 17, 2002 (SE) ................................................ 0200114

(51) Int. Cl.[7] .......................... A61M 16/00; A62B 7/00; F16K 31/02
(52) U.S. Cl. .......................... 128/204.22; 128/204.21; 128/204.26; 128/205.27; 128/207.12
(58) Field of Search ........................ 128/204.18, 204.19, 128/204.21, 204.22, 204.23, 204.26, 205.19, 205.24, 205.27, 207.12, 207.16

(56) References Cited

U.S. PATENT DOCUMENTS

| | | | | |
|---|---|---|---|---|
| 3,973,564 A | * | 8/1976 | Carden | 128/205.14 |
| 4,182,599 A | | 1/1980 | Eyrick et al. | |
| 5,400,778 A | | 3/1995 | Jonson et al. | |
| 5,492,115 A | * | 2/1996 | Abramov et al. | 128/205.24 |
| 5,611,335 A | * | 3/1997 | Makhoul et al. | 128/204.24 |
| 5,896,854 A | | 4/1999 | Bliss et al. | |
| 6,158,434 A | * | 12/2000 | Lugtigheid et al. | 128/204.22 |
| 6,279,574 B1 | * | 8/2001 | Richardson et al. | 128/204.18 |
| 6,298,848 B1 | | 10/2001 | Skog | |
| 6,308,703 B1 | | 10/2001 | Alving et al. | |

FOREIGN PATENT DOCUMENTS

FR 0 245 142 11/1987

OTHER PUBLICATIONS

Automatic Ventilation of the Lungs,: Mushin et al, Chapter 12: The Aika Respirator R–120 (1990) pp. 273–277.

* cited by examiner

Primary Examiner—Glenn K. Dawson
Assistant Examiner—Michael G. Mendoza
(74) Attorney, Agent, or Firm—Schiff Hardin LLP

(57) ABSTRACT

A device for reducing dead space in a ventilator system has a first tube connectable to the dead space in the ventilator system for producing a flow path for the transport of gas from dead space in the ventilator system, a suction device connected to the first tube for generating an adjustable negative pressure in the first tube, a second tube connectable to dead space in the ventilator system, for producing a flow path for the transport of gas to dead space in the ventilator system, a pump connected to the second tube for generating an adjustable positive pressure in the second tube, and a control unit which regulates the suction device and the pump. The suction device and the pump are formed by a first chamber and a second chamber, respectively, in an enclosure, separated by a gas-tight, moving partition. The control unit regulates the moving partition to regulate the suction device and the pump for achieving simpler and more reliable operation.

18 Claims, 2 Drawing Sheets

DEVICE FOR REDUCING DEAD SPACE IN A VENTILATOR SYSTEM

BACKGROUND OF THE INVENTION

1. Field of the Invention

The present invention relates to a device for reducing dead space in a ventilator system, as well as to a ventilator system employing such a device.

2. Description of the Prior Art

In the mechanical ventilation of a patient with a ventilator system (in intensive care, anesthesia etc.), an abnormal amount of dead space develops for the patient. The term "dead space" refers to the volume in which there is no gas exchange. As a result, expired gas in the dead space is returned to the patient at the next inspiration. The ventilator system's dead space mainly consists of the connection between a Y-piece and the patient (e.g. a tracheal tube and humidifier/heat exchanger and a measurement tube for measuring gas contents, flow, pressure etc.) Dead space can be relatively large, depending on the design of the ventilator system.

Since, as a rule, the last gas expired in every breath contains the highest concentration of carbon dioxide, the larger dead space causes greater re-breathing of carbon dioxide.

U.S. Pat. No. 5,400,778 describes a ventilator system containing a device for reducing the re-breathing of carbon dioxide. In one embodiment, gas is suctioned out of a tracheal tube while gas is delivered at the same time by the ventilator system through an inspiratory line. Additional gas can be supplied through additional connected lines, making it necessary to compensate the regulation of flows for the different volumes supplied to and evacuated from dead space.

Although the known device/ventilator system functions well, there is still a desire to achieve a device producing the same or equivalent effects with a simpler construction, especially with regard to control over-evacuated and delivered gas. Achieving a device that can be easily moved between different ventilator system, regardless of the design and application, would also be desirable. Another desire is to achieve a device that ensures simple maintenance of device functionality in the event of a power failure etc.

SUMMARY OF THE INVENTION

An object of the present invention is to provide a device that fulfills one or more of the aforementioned desires.

The above object is achieved in accordance with the principles of the present invention in a device for reducing dead space in a ventilation system having a first tube connectable to dead space in the ventilator system for producing a flow path for transport of gas from the dead space, a suction unit connected to the first tube for generating an adjustable negative pressure in the first tube, a second tube connectable to the dead space for producing a flow path for transport of gas to said dead space, a pump connected to the second tube for generating an adjustable positive pressure in the second tube, the suction unit and the pump being formed respectively by a first chamber and a second chamber in an enclosure with the first and second chambers being separated by a gas-tight, movable partition, and a control unit for regulating the suction unit and the pump by moving the partition.

A suction unit connected to a pump is achieved in an embodiment wherein enclosure is provided with two chambers separated by a moving partition. The interconnected suction unit and pump unit make it possible to achieve simultaneous evacuation and delivery of a selected volume of gas in a simple and effective fashion. The chambers are connected to dead space via the tubes, and the entire device is compact and easy to transport and move between different kinds of ventilator systems.

The first chamber can be devised with an evacuation unit in order to empty the suction means when the movable partition moves back and forth. In the corresponding manner, the second chamber can be devised with a gas connection for delivering fresh gas. Here, the gas connector can be connectable to the ventilator system. This provides the advantage that no separate gas supply is necessary.

When equipped with a signal input for receiving signals, the device is able to receive signals from the ventilator system. Especially signals indicating where the ventilator is in the breathing cycle. The device is for activation primarily during the end phase of expiration (or during a pause following expiration) in order to reduce dead space in the ventilator system.

Information about the breathing cycle can alternatively be obtained from a flow meter arranged in the ventilator system's expiratory components.

Increased accuracy in maintaining a volume of evacuated gas of the same magnitude as the volume of gas delivered is achieved by connecting a first manometer to the first tube or first chamber and a second manometer to the second tube or second chamber. For additional accuracy, pressure in dead space can be determined, either by means of a signal from the ventilator system or by a separate, third manometer connectable to the ventilator system's dead space. When the prevailing pressure (and pressure gradient) is(are) known, the device can be controlled to ensure that the volumes evacuated and delivered are virtually identical.

The device can be completely integrated into a ventilator system.

DESCRIPTION OF THE PREFERRED EMBODIMENTS

Figure 1:
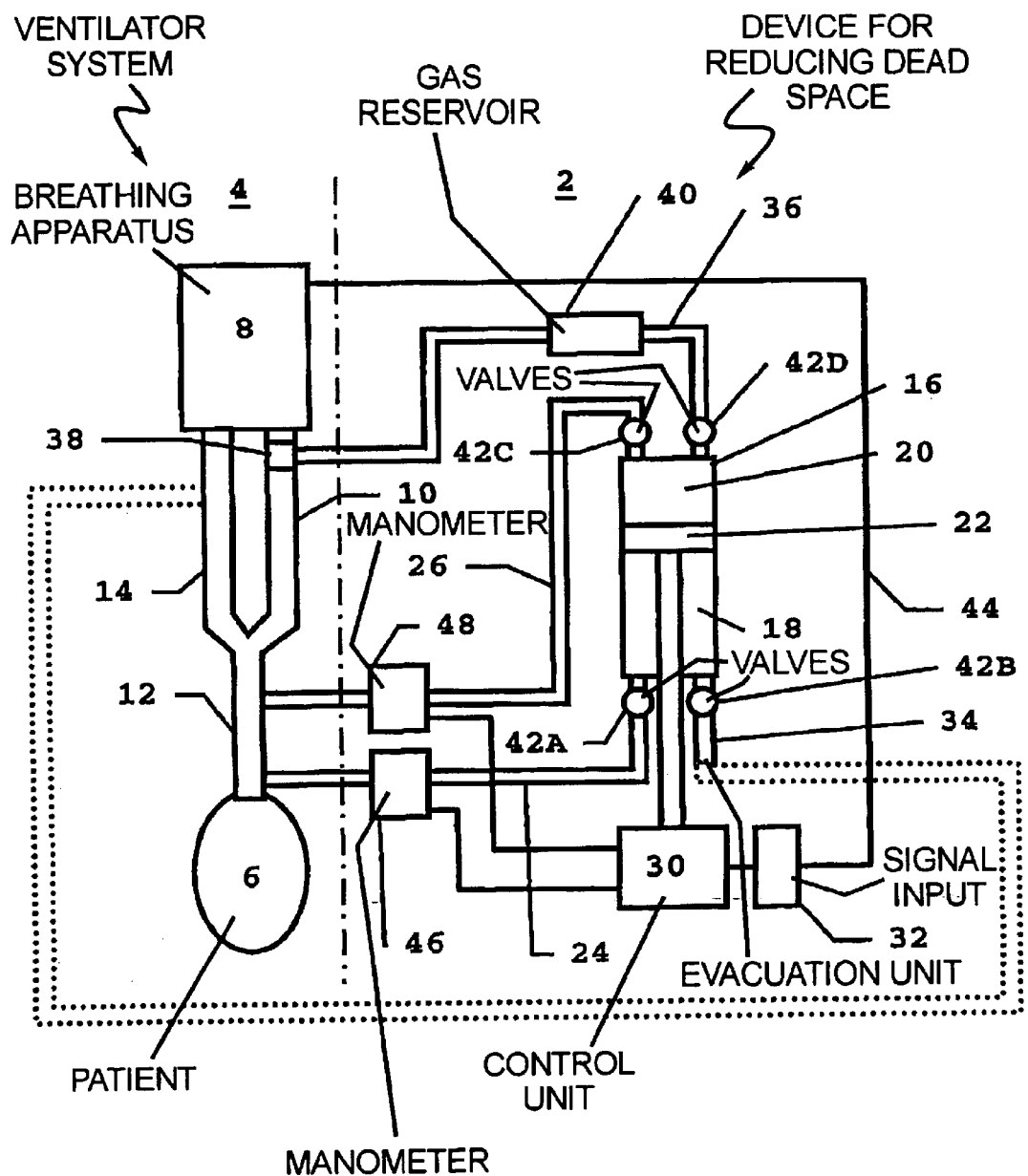
FIG. 1 shows a first embodiment of the inventive device connected to a ventilator system.

FIG. 1 is a general view of a device 2 according to the invention and a ventilator system 4. Here the dividing line designates a possible division between the device 2 and the ventilator system 4. This will be explained in detail below.

The ventilator system 4 can be connected to a patient 6 in order to facilitate, support or control the patient's 6 breathing. In principle, the ventilator system 4 here can consist of any breathing apparatus 8 that can be connected to an air-breathing creature (human or animal). A ventilator, respirator or an anesthetic machine in particular. The breathing apparatus 8 is equipped with a tubing system for connection to the patient 6. In this instance, the tubing system comprises an inspiratory tube 10, a patient connector 12 and an expiratory tube 14.

The dead space of the ventilator system 4 consists almost entirely of the patient connector 12. However, this is not the only volume which presents a re-breathing risk to the patient 6. To this must be added some or all of the patient's 6 dead space. The amount of added dead space of the patient 6 depends on the type of patient connector 12 used. As a rule, tracheal tubes and tracheotomy tubes cause some of the dead space of the patient 6 to disappear, whereas face masks and nasal connectors do not, as a rule, affect the dead space of the patient 6. The latter usually have a smaller dead space than the former, so the device according to the invention is most advantageous with patient connectors 12 such as tracheal tubes and tracheotomy tubes.

Other components can be connected to or be part of the patient connector 12. Humidifiers and heat exchangers (usually referred to as HME's) and measurement channels for flow measurement and/or gas analysis are examples of such components. As a rule, these components increase dead space.

The device 2 according to the first embodiment has an enclosure 16 with an interior subdivided into a first chamber 18 and a second chamber 20 by a movable partition 22.

The first chamber 18 is connectable to the patient connector 12 by a first tube 24, and the second chamber 20 is connectable to the patient connector 12 by a second tube 26. More exactly, the chambers 18, 20 are connectable to dead space.

The partition 22 is connected to a shaft 28 driven and regulated by a control unit 30 so it can be moved in a controlled manner. Any known power transmission unit, i.e. pneumatic, electromagnetic etc., is capable of actuating the shaft 28.

These components would actually suffice in the simplest version of the device 2. In an initial stage, the partition 22 could be arranged so the volume of the first chamber 18 is zero. The second chamber 20 could simultaneously be filled with fresh gas to a specific positive pressure in relation to an anticipated average pressure in dead space at the time of evacuation/replenishment. (In principle, this would correspond to the patient's 4 positive end expiratory pressure, i.e. PEEP.) In this position, the second chamber 20 would have a virtually maximal volume, e.g. two liters. The partition 22 could be moved a distance, for every evacuation/filling performed, corresponding to the volume to be evacuated from or added to dead space. With e.g. 20 milliliters as the volume to be withdrawn and replenished respectively, 100 evacuations/fillings could be performed (100 movement steps by the partition 22). It would then be necessary to detach the device 2 in order to return the partition 22 to its starting position (simultaneously emptying evacuated gas and supplying fresh gas.) A different number of evacuations/replenishments would naturally be needed with other volumes.

The timing of the point at which gas is withdrawn/replenished can be obtained from a signal input 32 for the control unit 30. Information on the breathing cycles is sent from the breathing apparatus 8 to the control unit 30 via a signal line 44.

However, the simplest version of the above would make it necessary for the device 2 to be devised with a relatively large volume. In addition, it would have to be periodically disconnected from the ventilator system 4. Disconnecting the embodiment of the device 2 shown in FIG. 1 from the ventilator system 4 in order to remove evacuated gas and replenish with fresh gas would not be necessary. The device 2 according to FIG. 1 can therefore operate on a somewhat varied principle in which gas replacement takes place after each evacuation/replenishment.

The device 2 is accordingly devised with an evacuation unit 34 for the first chamber 18 and a gas connector 36 for the second chamber 20. Evacuated gas can be discharged into atmosphere or connected to the expiratory tube 14 (preferably close to the breathing apparatus 8, shown with a dotted line in FIG. 1) or some special device for collecting gas. The gas connector 36 is connected to the inspiratory tube 10 via a valve 38 and a gas reservoir 40. The gas reservoir 40 is not inherently necessary. In many instances, especially when the ventilator system is devised for adult patients, the inspiratory tube 10 holds a sufficiently large volume of gas to fill the second chamber 20. The risk of expired gas being sucked into the inspiratory tube 10, thereby contributing to re-breathing of carbon dioxide, can be avoided by, e.g. adding a bias flow of gas through the inspiratory tube 10 and expiratory tube 14.

When evacuation/replenishment are to occur, the partition 22 is moved forward (upward in FIG. 1), causing negative pressure to develop in the first chamber 18 and positive pressure to develop in the second chamber 20. The pressure gradient between the respective chambers 18, 20 and dead space (the patient connector 12) gives rise to a flow of expired gas to the first chamber 18 and a flow of fresh gas to dead space.

After evacuation/replenishment have been concluded, the partition is returned to its starting position (advantageously in the end position against the first chamber 18, i.e. at the bottom of FIG. 1). Evacuated gas is now forced out into atmosphere (or to a separate vacuum evacuation unit or to the expiratory tube 14, which is suitable when the gas contains an anesthetic or other gases that should not be discharged directly) via the evacuation unit 34. At the same time, the second chamber 20 is filled with fresh gas via the gas connector 36. This can take place at a suitable point in the breathing cycle, e.g. during the introductory phase of an expiration (i.e. after the inspiratory phase following the evacuation/replenishment.)

The exact times for evacuation and replenishment respectively can vary in the patient connector 12 and even be arranged in the patient 4 below the patient connector 12. Even if the figure schematically depicts evacuation closer to the patient 4 than replenishment, the reverse circumstance can be employed, i.e. replenishment of fresh gas closer to the patient 4 (or deeper inside the patient 4) than evacuation.

Even though evacuation/replenishment in each breathing cycle would be advantageous with movement of the partition 22 (e.g. from one end position to the other end position, like a piston stroke), a number of other options is conceivable if the volume to be withdrawn/replenished must be greater than the volume achievable with a partition movement. Thus, this implies that the entire device can be made very compact and operate continuously with a number of "piston strokes" for each breathing cycle. With a volume of 10 ml in every "piston stroke" and evacuation of 20 ml in each breathing cycle, for example, two "piston strokes" would be required etc. The advantage of a compact (small and light) device 2 is that it can be placed very close to the patient 4, enabling the use of much shorter tubes 24, 26.

It is evident that the size of the device 2 can vary considerably. The simple version previously described could conceivably hold up to 5 liters of fresh gas or more, whereas the compact version could hold a volume of fresh gas of 10 milliliters or less. Especially in respect to the smaller volumes, other ways of moving the partition are obviously available. For example, the partition could be a shuttle, activated by electromagnetic means, able to move between end positions. A roller membrane moved between two positions could work as well as a piston and possibly even display less friction resistance. In other words, all known pumping principles can be applied to this invention.

The valve 38 is intended for switching the gas outlet on the breathing apparatus 8 to enable the gas reservoir 40 (or second chamber 20) to fill with gas on a periodic basis, preferably during expiration phases. The valve 38 can be devised to divert only part of the total flow when diverting gas from the inspiratory tube 10 during the inspiratory phase. Or it can change the entire gas flow for brief periods of time. In some modern breathing machines 8, the latter methods may present certain regulatory problems and the generation of needless alarms. This can be avoided by returning withdrawn gas to the expiratory line 14 from the evacuation unit 34. This would then result in a closed system for the device 2 in relation to the breathing apparatus 8. If the breathing apparatus 8 contains a separate second gas outlet, this outlet could be used.

The gas reservoir 40, preferably formed by a bellows or some other variable-volume container, mainly makes it possible for the second chamber 20 to be filled to the same gas pressure (adjustable) in each replenishment. This gas pressure obviously does not need to be identical to the pressure of the gas diverted from the inspiratory line 10. Compression or decompression can take place in the gas reservoir 40 before or in conjunction with the filling of the second chamber 20.

For complete transferability between different ventilator systems 4, the valve 38 should be part of the device 2 and devised as an adapter that can be connected onto the inspiratory line 10. Here, it does not matter if the valve 38 is devised with a variable connection diameter or if the device 2 is equipped with multiple valves 38, each of which devised for connection to a specific tube diameter (for the inspiratory line 10.)

A first valve 42A is arranged at the first tube 24, a second valve 42B is arranged at the evacuation unit 34, a third valve 42C is arranged at the second tube 26 and a fourth valve 42D is arranged at the gas connector 36 to ensure that gases flow in the right direction. The valves 42A, 42B, 42C, 42D can be check valves.

A first manometer 46 is arranged to measure pressure in the first tube 24, and a second manometer 48 is arranged to measure pressure in the second tube 26 in order to increase accuracy in ensuring agreement of the volumes withdrawn and replenished. In principle, one of the manometers 46, 48 may suffice, but two would convey additional reliability and accuracy. It should be noted that the manometers 46, 48 are by no means essential components. Sufficient accuracy can be achieved without them.

During periods in breathing cycles in which the device 2 is inactive (is evacuating/replenishing), flow is null in the tubes 24, 26. Placement of the manometers 46, 48 in the tubes 24, 26 (instead of in the chambers 18, 20) makes it possible to even measure pressure in dead space (the patient connector 12). Measured pressure could therefore be used as an indication of the course of the breathing cycle, i.e. be used for determining when evacuation/replenishment should take place.

Figure 2:
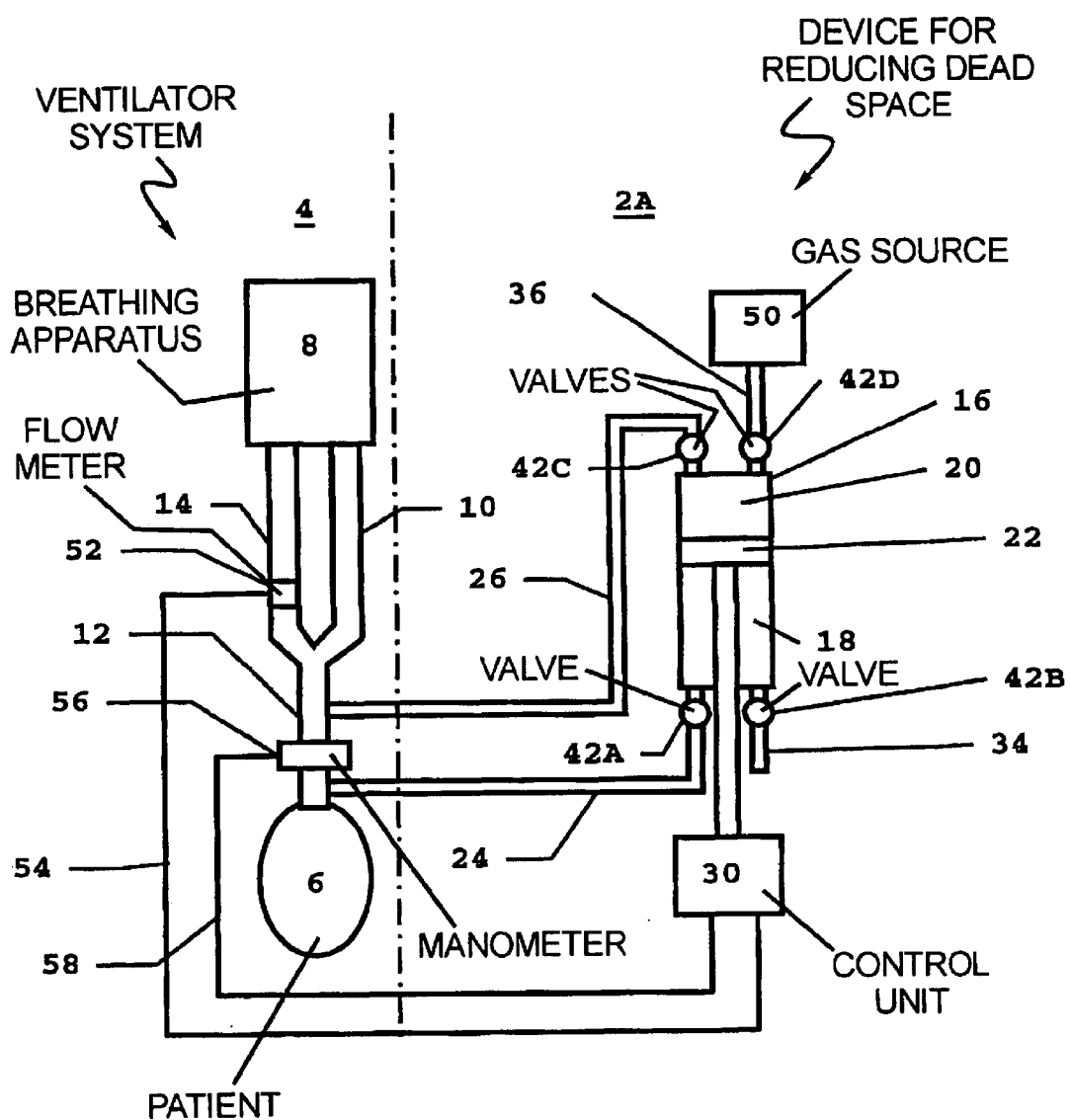
FIG. 2 shows a second embodiment of the inventive device connected to a ventilator system.

A second embodiment of the device 2A is shown in FIG. 2. Components and parts that can be identical have been retained with the same designations as in FIG. 1.

The statements above in connection with FIG. 1 apply to the components that are identical therewith in FIG. 2. In principle, the differences between the embodiments are as follows.

The device 2A illustrates a separate gas source 50 for adding fresh gas to the second chamber 20. The separate gas source 50 can consist of a gas cylinder, a compressor, a pump, a wall gas connection or ambient air. This conveys special advantages in cases in which a gas composition other than the one supplied by the breathing apparatus 8 must be initially supplied to the patient 6. This other gas composition can be everything from another concentration composition of the gases (e.g. a higher concentration of oxygen) delivered by the breathing apparatus 8 to completely different compositions (medical gases, medication etc.)

A flow meter 52 is devised for placement in the expiratory line 14, e.g. by means of a tube adapter. The flow meter 52 supplies information on the breathing cycles. The measurement signal is sent to the control unit 30 via a first measurement line 54.

A third manometer 56 is arranged to measure the pressure in dead space. The measurement signal is sent to the control unit 30 via a second measurement line 58.

There are further versions of means for controlling the device 2, 2A in addition to those set forth above.

For example, the evacuation unit 34 can be connected to a vacuum source in order to achieve a constant negative pressure reinforcing the negative pressure generated in the first chamber 18 when the partition 22 moves. This can be used when large amounts of gas must be withdrawn or if the volume of replenished gas is harder to regulate because of the pressure of fresh gas at the gas connector 36.

Alternatively, the evacuation unit 34 can be used to admit gas into the first chamber 18 at the same time as it sucks gas out of dead space. This can be used when small volumes are desired (instead of regulating stroke length, moving the partition 22 etc.) or if replenished gas is harder to regulate because of the pressure of fresh gas at the gas connector 36.

Conversely, the gas connector 36 can be used in the corresponding fashion. In these functional versions, it would be advantageous (sometimes necessary) for one or more of the valves 42A, 42B, 42C, 42D to e adjustable valves rather than check valves. Adjustable valves may also be used if certain time delays are desired in evacuation/replenishment. For example, evacuation can be initiated a few milliseconds before replenishment and vice versa.

The two described embodiments (including described alternate versions) are fully combinable with respect to components and functions.

Another advantage of the device 2, 2A is that the risk of an adverse impact on the lung is reduced (compensation is automatically made for evacuated gas, thereby avoiding hazardous negative pressure).

Humidification of the fresh gas has not been addressed above. In principle, gas evacuation could cause the extraction of moisture from the patient. Humidifying fresh gas in a known way before replenishment or after fresh gas is pumped into the patient connector 12 can compensate for this. In the device 2A in FIG. 2, the gas supplied separately from a gas source 50 can be humidified gas.

The tubes 24, 26, and their connection to the patient connector 12 can be devised in a number of ways. For example, the tubes 24, 26 may be catheters inserted into the patient connector 12 at the transition to the inspiratory line 10 and the expiratory line 14. One of the tubes 24, 26 (the catheter) can then be introduced more deeply (into) the patient 4 than the other. If the first tube 24 is introduced more deeply into the patient, it can also transport mucous and secretion from the patient 4 (and accordingly make separate mucous removal unnecessary.) Alternatively, the patent connector 12 can be devised with channels for the different functions, and tubes 24, 26 can be connected to these channels.

A combination of the two (a catheter and a channel) is also possible.

It should be noted that e.g. tracheal tubes with multiple lumina are well-known in the ventilator field.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for reducing dead space in a ventilator system, comprising:
   a first tube adapted for connection to dead space in a ventilator system for producing a flow path for transport of gas from said dead space;
   a suction unit connected to said first tube for generating an adjustable negative pressure in said first tube;
   a second tube adapted for connection to said dead space for producing a flow path for transport of gas to said dead space;
   a pump connected to said second tube for generating an adjustable positive pressure in said second tube;
   said suction unit and said pump being formed respectively by a first chamber and a second chamber in an enclosure, said first and second chambers being separated by a gas-tight, movable partition; and
   a control unit for regulating said suction unit and said pump by moving said partition.

2. A device as claimed in claim 1 further comprising an evacuation unit in fluid communication with said first chamber for evacuated gas, and a gas connector in fluid communication with said second chamber for gas replenishment.

3. A device as claimed in claim 2 wherein said evacuation unit is adapted for connection to said ventilator system.

4. A device as claimed in claim 2 wherein said gas connector is adapted for connection to said ventilator system.

5. A device as claimed in claim 1 wherein said control unit has a signal input adapted to receive signals from said ventilator system, and wherein said control unit regulates said suction unit and said pump dependent on said signals.

6. A device as claimed in claim 1 further comprising a manometer in fluid communication with one of said first tube and said first chamber and generating a manometer output supplied to said control unit, and wherein said control unit regulates said suction unit and said pump dependent on said manometer output.

7. A device as claimed in claim 1 further comprising a manometer in fluid communication with one of said second tube and said second chamber and generating a manometer output supplied to said control unit, and wherein said control unit regulates said suction unit and said pump dependent on said manometer output.

8. A device as claimed in claim 1 further comprising a first manometer in fluid communication with one of said first tube and said first chamber which generates a first manometer output, a second manometer in fluid communication with one of said second tube and said second chamber which generates a second manometer output, said first and second manometer outputs being supplied to said control unit, and wherein said control unit regulates said suction unit and said pump dependent on said first and second manometer outputs.

9. A device as claimed in claim 1 further comprising a manometer adapted for connection to said ventilator system adapted to determine a pressure in said dead space, said manometer generating a manometer output, and wherein said control unit regulates said suction unit and said pump dependent on said manometer.

10. A ventilator system as claimed in claim 1 further comprising a manometer adapted for connection to said ventilator system adapted to determine a pressure in said dead space, said manometer generating a manometer output, and wherein said control unit regulates said suction unit and said pump dependent on said manometer.

11. A ventilator system as claimed in claim 1 further comprising an evacuation unit in fluid communication with said first chamber for evacuated gas, and a gas connector in fluid communication with said second chamber for gas replenishment.

12. A ventilator system as claimed in claim 2 wherein said evacuation unit is adapted for connection to said ventilator system.

13. A ventilator system as claimed in claim 2 wherein said gas connector is adapted for connection to said ventilator system.

14. A ventilator system as claimed in claim 1 wherein said control unit has a signal input adapted to receive signals from said ventilator system, and wherein said control unit regulates said suction unit and said pump dependent on said signals.

15. A ventilator system as claimed in claim 1 further comprising a manometer in fluid communication with one of said first tube and said first chamber and generating a manometer output supplied to said control unit, and wherein said control unit regulates said suction unit and said pump dependent on said manometer output.

16. A ventilator system as claimed in claim 1 further comprising a manometer in fluid communication with one of said second tube and said second chamber and generating a manometer output supplied to said control unit, and wherein said control unit regulates said suction unit and said pump dependent on said manometer output.

17. A ventilator system as claimed in claim 1 further comprising a first manometer in fluid communication with one of said first tube and said first chamber which generates a first manometer output, a second manometer in fluid communication with one of said second tube and said second chamber which generates a second manometer output, said first and second manometer outputs being supplied to said control unit, and wherein said control unit regulates said suction unit and said pump dependent on said first and second manometer outputs.

18. A ventilator system, comprising:
   a first tube adapted for connection to dead space in a ventilator system for producing a flow path for transport of gas from said dead space;
   a suction unit connected to said first tube for generating an adjustable negative pressure in said first tube;
   a second tube adapted for connection to said dead space for producing a flow path for transported gas to said dead space;
   a pump connected to said second tube for generating an adjustable positive pressure in said second tube;
   said suction unit and said pump being formed respectively by a first chamber and a second chamber in an enclosure, said first and second chambers being separated by a gas-tight, movable partition; and
   a control unit for regulating said suction unit and said pump by moving said partition.

* * * * *